US009138359B2

(12) United States Patent
Isele et al.

(10) Patent No.: US 9,138,359 B2
(45) Date of Patent: *Sep. 22, 2015

(54) HYGIENE ARTICLES CONTAINING NANOFIBERS

(71) Applicant: The Procter & Gamble Company, Cincinnati, OH (US)

(72) Inventors: Olaf Erik Alexander Isele, West Chester, OH (US); Rajeev Chhabra, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/625,952

(22) Filed: Sep. 25, 2012

(65) Prior Publication Data

US 2013/0023836 A1    Jan. 24, 2013

(51) Int. Cl.
 A61F 13/514    (2006.01)
 A61F 13/15     (2006.01)
 A61F 13/537    (2006.01)
 D04H 13/00     (2006.01)
 D04H 13/02     (2006.01)

(52) U.S. Cl.
 CPC .......... *A61F 13/514* (2013.01); *A61F 13/15658* (2013.01); *A61F 13/5146* (2013.01); *A61F 13/537* (2013.01); *D04H 13/002* (2013.01); *D04H 13/02* (2013.01)

(58) Field of Classification Search
 CPC ............ A61F 2013/51445; A61F 2013/51447; A61F 13/5146
 USPC ....................... 604/367, 370, 385.3
 See application file for complete search history.

(56) References Cited

U.S. PATENT DOCUMENTS

| | | | |
|---|---|---|---|
| 3,280,229 A | 10/1966 | Simons | |
| 3,475,198 A | 10/1969 | Drum | |
| 3,806,289 A | 4/1974 | Schwarz | |
| 3,849,241 A | 11/1974 | Butin et al. | |
| 3,972,759 A | 8/1976 | Buntin | |
| 3,989,867 A * | 11/1976 | Sisson ........................... 428/132 | |
| 4,100,324 A | 7/1978 | Anderson et al. | |
| 4,536,361 A | 8/1985 | Torobin | |
| 4,587,154 A | 5/1986 | Hotchkiss et al. | |
| 4,713,068 A | 12/1987 | Wang et al. | |
| 4,753,843 A | 6/1988 | Cook et al. | |
| 4,784,892 A | 11/1988 | Storey et al. | |
| 4,818,464 A | 4/1989 | Lau | |
| 4,824,451 A | 4/1989 | Vogt et al. | |
| 4,869,275 A | 9/1989 | Berger | |
| 4,874,666 A | 10/1989 | Kubo et al. | |
| 4,919,810 A | 4/1990 | Itoh et al. | |
| 4,923,454 A | 5/1990 | Seymour et al. | |
| 4,937,020 A | 6/1990 | Wagner et al. | |
| 4,973,325 A | 11/1990 | Sherrod et al. | |
| 4,980,215 A | 12/1990 | Schonbrun | |
| 5,039,727 A | 8/1991 | Onishi et al. | |
| 5,075,161 A | 12/1991 | Nyssen et al. | |
| 5,108,820 A | 4/1992 | Kaneko et al. | |
| 5,114,631 A | 5/1992 | Nyssen et al. | |
| 5,137,600 A | 8/1992 | Barnes et al. | |
| 5,183,670 A | 2/1993 | Trudeau et al. | |
| 5,192,468 A | 3/1993 | Coates et al. | |
| 5,213,881 A | 5/1993 | Timmons et al. | |
| 5,244,482 A | 9/1993 | Hassenboehler et al. | |
| 5,260,003 A | 11/1993 | Nyssen et al. | |
| 5,290,626 A | 3/1994 | Nishioi et al. | |
| 5,464,688 A | 11/1995 | Timmons et al. | |
| 5,482,765 A | 1/1996 | Bradley et al. | |
| 5,487,943 A | 1/1996 | Kozulla | |
| 5,518,801 A | 5/1996 | Chappell et al. | |
| 5,679,042 A | 10/1997 | Varona | |
| 5,679,379 A | 10/1997 | Fabbricante et al. | |
| 5,681,646 A | 10/1997 | Ofosu et al. | |
| 5,695,849 A | 12/1997 | Shawver et al. | |
| 5,700,254 A | 12/1997 | McDowall et al. | |
| 5,733,822 A | 3/1998 | Gessner et al. | |
| 5,843,056 A | 12/1998 | Good et al. | |
| 5,885,269 A | 3/1999 | Boyer et al. | |
| 5,885,681 A | 3/1999 | Korpman | |

(Continued)

FOREIGN PATENT DOCUMENTS

| | | |
|---|---|---|
| JP | Hei 01-156561 | 6/1989 |
| JP | 3249207 A2 | 11/1991 |
| JP | 06-192953 | 7/1994 |
| JP | 06-192954 | 7/1994 |
| JP | 08-144166 A | 6/1996 |
| JP | 2668963 B2 | 10/1997 |
| JP | 2001-104372 A | 4/2001 |
| JP | 2002-201560 | 7/2002 |

(Continued)

OTHER PUBLICATIONS

Fiber Handbook, Raw Materials, III, Production section (II), Edited by the Fiber Society, Maruzen Co., Ltd., 1970.
Notice of opposition to a European patent filed by Fiberweb Corovin GmbH, filed Nov. 25, 2011, 38 pages.
Notice of opposition to a European patent filed by Borealis AG, filed Dec. 2, 2011, 25 pages.
Notice of opposition to a European patent filed by Paul-Hartmann-AG, filed Nov. 28, 2011, 14 pages.

*Primary Examiner* — Melanie Hand
*Assistant Examiner* — Paula L Craig
(74) *Attorney, Agent, or Firm* — Sarah M. DeCristofaro; Jeffrey V. Bamber; Angela M. Stone

(57) ABSTRACT

A method of making a nonwoven web comprising nanofibers that are made by a melt film fibrillation process is disclosed. The nanofibers have a diameter of less than 1 micron, and comprise a significant number of the fibers in one layer of the web. The process generally includes the steps of providing a polymeric melt, utilizing a central fluid stream to form an elongated hollow polymeric film tube, and using this and/or other fluid streams to form multiple nanofibers from the hollow tube.

22 Claims, No Drawings

(56) References Cited

U.S. PATENT DOCUMENTS

| | | | |
|---|---|---|---|
| 5,910,368 A | 6/1999 | Ehret | |
| 5,935,883 A | 8/1999 | Pike et al. | |
| 5,939,467 A | 8/1999 | Wnuk et al. | |
| 5,977,250 A | 11/1999 | George et al. | |
| 5,994,482 A | 11/1999 | Georgellis et al. | |
| 6,110,588 A | 8/2000 | Perez et al. | |
| 6,114,017 A | 9/2000 | Fabbricante et al. | |
| 6,183,670 B1 | 2/2001 | Torobin et al. | |
| 6,187,699 B1 | 2/2001 | Terakawa et al. | |
| 6,258,997 B1 | 7/2001 | Johansson et al. | |
| 6,265,333 B1 | 7/2001 | Dzenis et al. | |
| 6,269,513 B1 | 8/2001 | Torobin | |
| 6,284,680 B1 | 9/2001 | Aikawa | |
| 6,315,806 B1 | 11/2001 | Torobin et al. | |
| 6,331,343 B1 | 12/2001 | Perez et al. | |
| 6,350,711 B1 | 2/2002 | Potts et al. | |
| 6,382,526 B1 | 5/2002 | Reneker et al. | |
| 6,395,046 B1 | 5/2002 | Emig et al. | |
| 6,432,347 B1 | 8/2002 | Perez et al. | |
| 6,464,994 B1 | 10/2002 | Moehring | |
| 6,488,801 B1 | 12/2002 | Bodaghi et al. | |
| 6,494,974 B2 | 12/2002 | Riddell | |
| 6,520,425 B1 | 2/2003 | Reneker | |
| 6,613,703 B1 | 9/2003 | Yahiaoui et al. | |
| 6,692,823 B2 | 2/2004 | Kody et al. | |
| 6,695,992 B2 | 2/2004 | Reneker | |
| 6,706,086 B2 | 3/2004 | Emig et al. | |
| 6,872,311 B2 | 3/2005 | Koslow | |
| 6,878,650 B2 | 4/2005 | Clark et al. | |
| 6,924,028 B2 | 8/2005 | Chung et al. | |
| 7,097,904 B2 | 8/2006 | Ochi et al. | |
| 7,267,789 B2 | 9/2007 | Chhabra et al. | |
| 7,291,300 B2 | 11/2007 | Chhabra et al. | |
| 7,390,760 B1 | 6/2008 | Chen et al. | |
| 7,576,019 B2 | 8/2009 | Bond et al. | |
| 7,989,369 B2 | 8/2011 | Bond et al. | |
| 8,395,016 B2 * | 3/2013 | Isele et al. | 604/367 |
| 8,487,156 B2 * | 7/2013 | Isele et al. | 604/367 |
| 8,835,709 B2 * | 9/2014 | Isele et al. | 604/367 |
| 2001/0027303 A1 * | 10/2001 | Bewick-Sonntag | 604/381 |
| 2002/0006434 A1 | 1/2002 | Shanklin et al. | |
| 2002/0035354 A1 | 3/2002 | Mirle et al. | |
| 2002/0046656 A1 | 4/2002 | Benson et al. | |
| 2002/0096246 A1 | 7/2002 | Sennet et al. | |
| 2002/0110655 A1 | 8/2002 | Seth | |
| 2002/0117782 A1 | 8/2002 | Haynes et al. | |
| 2002/0129834 A1 | 9/2002 | Bailey | |
| 2002/0148050 A1 | 10/2002 | Luo et al. | |
| 2003/0065298 A1 | 4/2003 | Krishnaswamy-Mirle et al. | |
| 2003/0129909 A1 | 7/2003 | Zucker | |
| 2003/0168401 A1 | 9/2003 | Koslow | |
| 2003/0177909 A1 | 9/2003 | Koslow | |
| 2004/0002273 A1 | 1/2004 | Fitting et al. | |
| 2004/0031749 A1 | 2/2004 | Koslow | |
| 2004/0038013 A1 | 2/2004 | Schaefer et al. | |
| 2004/0070118 A1 | 4/2004 | Czado | |
| 2004/0092185 A1 | 5/2004 | Grafe et al. | |
| 2004/0116028 A1 | 6/2004 | Bryner | |
| 2004/0131820 A1 | 7/2004 | Turner et al. | |
| 2004/0223040 A1 | 11/2004 | Graham et al. | |
| 2004/0266300 A1 | 12/2004 | Isele et al. | |
| 2005/0008776 A1 | 1/2005 | Chhabra et al. | |
| 2005/0053782 A1 | 3/2005 | Sen et al. | |
| 2005/0070866 A1 | 3/2005 | Isele et al. | |
| 2006/0014460 A1 | 1/2006 | Isele et al. | |
| 2006/0057350 A1 | 3/2006 | Ochi et al. | |
| 2006/0057922 A1 | 3/2006 | Bond et al. | |
| 2006/0084340 A1 | 4/2006 | Bond et al. | |
| 2006/0094320 A1 | 5/2006 | Chen et al. | |
| 2006/0153904 A1 | 7/2006 | Smith et al. | |
| 2007/0021021 A1 | 1/2007 | Verdegan et al. | |
| 2010/0305529 A1 | 12/2010 | Ashton et al. | |
| 2011/0196325 A1 | 8/2011 | Isele et al. | |
| 2011/0196327 A1 | 8/2011 | Chhabra et al. | |
| 2011/0196332 A1 | 8/2011 | Cheng et al. | |
| 2013/0147080 A1 * | 6/2013 | Isele et al. | 264/115 |

FOREIGN PATENT DOCUMENTS

| | | |
|---|---|---|
| WO | WO-97/05306 | 2/1997 |
| WO | WO 00/22207 | 4/2000 |
| WO | WO 00/44411 | 8/2000 |
| WO | WO 00/71797 A1 | 11/2000 |
| WO | WO 01/00124 A1 | 1/2001 |
| WO | WO-01/09425 A1 | 2/2001 |
| WO | WO 01/97731 | 12/2001 |
| WO | WO-02092339 A1 | 11/2002 |
| WO | WO 03/043809 A1 | 5/2003 |
| WO | WO-03086234 A | 10/2003 |
| WO | WO 2004/020722 | 3/2004 |
| WO | WO-2004/026167 A2 | 4/2004 |
| WO | WO-2005004769 A | 1/2005 |
| WO | WO-2005005704 | 1/2005 |
| WO | WO-2005/103357 A1 | 11/2005 |

* cited by examiner

HYGIENE ARTICLES CONTAINING NANOFIBERS

FIELD OF THE INVENTION

The present invention relates to hygiene articles made from nanofibers and benefits of the hygiene articles.

BACKGROUND OF THE INVENTION

The need for articles produced from nonwoven containing nanofibers has continued to increase. The diameters of nanofibers are generally understood to be less than about 1000 nanometer or one micron. The nanofibers webs are desired due to their high surface area, low pore size, and other characteristics. The nanofibers, also commonly called microfibers or very fine fibers, can be produced by a variety of methods and from a variety of materials. Although several methods have been used, there are drawbacks to each of the methods and producing cost effective nanofibers has been difficult. Therefore, hygiene articles and other disposable consumer products containing nanofibers have not been marketed.

Methods of producing nanofibers include a class of methods described by melt fibrillation. Melt fibrillation is a general class of making fibers defined in that one or more polymers are molten and extruded into many possible configurations, such as co-extrusion, homogeneous or bicomponent films or filaments, and then fibrillated or fiberized into fibers. Non-limiting examples of melt fibrillation methods include melt blowing, melt film fibrillation, and melt fiber bursting. Methods of producing nanofibers, not from melts, are film fibrillation, electro-spinning, and solution spinning. Other methods of producing nanofibers include spinning a larger diameter bicomponent fiber in an islands-in-the-sea, segmented pie, or other configuration where the fiber is further processed after the fiber has solidified so that nanofibers result.

Melt blowing is a commonly used method of producing fibers. Typical fiber diameters range from 2 to 8 micron. Melt blowing can be used to make fibers with smaller diameters but with considerable changes needed to the process. Commonly, redesigned nozzles and dies are needed. Examples of these include U.S. Pat. Nos. 5,679,379 and 6,114,017 by Fabbricante et al. and U.S. Pat. Nos. 5,260,003 and 5,114,631 by Nyssen et al. These methods utilize relatively high pressures, temperatures, and velocities to achieve the small fiber diameter.

Melt film fibrillation is another method to produce fibers. A melt film tube is produced from the melt and then a fluid is used to form nanofibers from the film tube. Two examples of this method include Torobin's U.S. Pat. Nos. 6,315,806; 5,183,670; and 4,536,361; and Reneker's U.S. Pat. Nos. 6,382,526 and 6,520,425, assigned to the University of Akron. Although these methods are similar by first forming a melt film tube before the nanofibers result, the processes use different temperatures, flow rates, pressures, and equipment.

Film fibrillation is another method of producing nanofibers although not designed for the production of polymeric nanofibers to be used in nonwoven webs. U.S. Pat. No. 6,110, 588 by Perez et al., assigned to 3M, describes of method of imparting fluid energy to a surface of a highly oriented, highly crystalline, melt-processed polymer film to form nanofibers. The films and fibers are useful for high strength applications such as reinforcement fibers for polymers or cast building materials such as concrete.

Electrospinning is a commonly used method of producing nanofibers. In this method, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing nanofibers is solution or flash spinning which utilizes a solvent.

Two-step methods of producing nanofibers are also known. A two-step method is defined as a method of forming fibers in which a second step occurs after the average temperature across the fiber is at a temperature significantly below the melting point temperature of the polymer contained in the fiber. Typically, the fibers will be solidified or mostly solidified. The first step is to spin a larger diameter multicomponent fiber in an islands-in-the-sea, segmented pie, or other configuration. The larger diameter multicomponent fiber is then split or the sea is dissolved so that nanofibers result in the second step. For example, U.S. Pat. No. 5,290,626 by Nishio et al., assigned to Chisso, and U.S. Pat. No. 5,935,883, by Pike et al., assigned to Kimberly-Clark, describe the islands-in-the-sea and segmented pie methods respectively. These processes involve two sequential steps, making the fibers and dividing the fibers.

It is desired to produce a

To produce disposable hygiene articles containing nanofibers that are commercially advantageous, the cost of the nanofibers must be controlled. Equipment cost, process costs, any additional process aids, and polymer costs are all areas where costs can be controlled. Therefore, it is an object of the invention to produce nanofibers which are low in cost.

It is also desired to form hygiene products containing nanofibers for a variety of uses and benefits. The uses include as executions such as a diaper, wipe, and absorbent material, among other uses.

SUMMARY OF THE INVENTION

The present invention is directed to hygiene articles comprising nanofibers. The hygiene articles include diapers, training pants, adult incontinence pads, catamenials products such as feminine care pads and pantiliners, tampons, personal cleansing articles, personal care articles, and personal care wipes including baby wipes, facial wipes, body wipes, and feminine wipes. The nanofiber webs can be used as a barrier, wipe, absorbent material, and other uses. Particularly, the nanofiber web is used in a diaper as a liquid barrier, outer-cover, and/or leg cuff. It may also be used as a wipe for reducing the gradient of liquid, controlled delivery of materials, and other uses.

The nanofibers, having a diameter of less than 1 micron, must comprise a significant number of the fibers, preferably greater than 50% of fibers, in one layer of the web contained by the hygiene article. The nanofibers are produced from a melt film fibrillation process. The process generally includes the steps of providing a polymeric melt, utilizing a central fluid stream to form an elongated hollow polymeric film tube, and using this and/or other fluid streams to form multiple nanofibers from the hollow tube.

DETAILED DESCRIPTION OF THE INVENTION

The present invention relates to hygiene articles made from nanofibers. The nanofibers are produced from one or more thermoplastic polymers. Nonlimiting examples of thermoplastic polymers suitable for the present invention include polyolefins, polyesters, polyamides, polystyrenes, polyurethanes, biodegradable polymers including thermoplastic starch, PHA, PLA, starch compositions, and combinations thereof. The homopolymer, copolymers, and blends thereof are included within this description. The most preferred polymers are polyolefins such as polypropylene, polyethylene, nylons, and polyethylene terephthalate.

Suitable thermoplastic polymers include any polymer suitable for melt spinning. The rheological properties of the polymer must be such that the polymer can be melt extruded and is able to form a film. The melting temperature of the polymer is generally from about 25° C. to 400° C. The polymers of the present invention as they are present in the die may have a melt flow rate of less than about 400 decigrams per minute. The melt flow rate is measured using ASTM method D-1238. Preferably, the melt flow rate may be less than about 300 decigrams per minute, more preferably less than about 200 decigrams per minute, and most preferably less than about 100 decigrams per minute. A most preferred range for melt flow rates is from about 1 decigram per minute to about 100 decigrams per minute. Generally, the lower the melt flow rate the more preferred. Therefore, polymers with melt flow rates less than about 50 decigrams per minute and 40 decigrams per minute may be utilized.

The fibers may be single or multicomponent fibers such as bicomponent fibers. The fibers may have a sheath-core or side-by-side or other suitable geometric configuration. After the fibers are made, the fibers may be treated or coated before formed into a web. Additionally, after a web is made, the web may be treated. Optionally, additives may be compounded into the polymer resin and these additives may move out to the surface of the fiber after the fibers are formed. The additives that migrate to the surface may need to be cured utilizing external energy, such as heat, or additives on surface may need to be chemically reacted with another component or curing may need to be catalyzed in the presence of another component, such that additional components may be added to the process while the fibers are being made or after the fibers are made using the resin with additives. Suitable treatments include hydrophilic or hydrophobic treatments. An example of hydrophobic treatment is poly-di-methyl-siloxanes. The specific treatment depends on the use of the web, type of polymer, and other factors.

Optionally, the polymer may contain additional materials to provide other properties for the fiber. These may modify the physical properties of the resulting fiber such as elasticity, strength, thermal or chemical stability, appearance, absorbency, odor absorbency, surface properties, and printability, among others. A suitable hydrophilic melt additive may be added. Optional materials may be present up to 50% of the total polymer composition.

The method of making the nanofibers of the present invention is a melt fibrillation process and more preferably a melt film fibrillation process. Generally, a melt film fibrillation process involves providing a polymeric melt, utilizing a central fluid stream to form an elongated hollow polymeric film tube, and then using a fluid to form multiple nanofibers from the hollow tube. Suitable methods are detailed, for example, in U.S. Pat. No. 4,536,361 to Torobin and U.S. Pat. Nos. 6,382,526 and 6,520,425 to Reneker. The melt film fibrillation methods can utilize various different processing conditions. Reneker's method more specifically includes the steps of feeding the polymer into an annular column and forming a film or tube at the exit of the annular column where a gas jet space is formed. A gas column then provides pressures on the inner circumference of the polymer tube. When the polymer tube exits the gas jet space, it is blown apart into many small fibers, including nanofibers, due to the expanding central gas.

An example of a melt film fibrillation method more specifically includes the steps of melting the polymer to form a polymeric melt. The polymeric melt will contain the polymer composition and any other ingredients. The polymeric melt is extruded through an orifice which in turn contains a central fluid stream such that the polymer extrudes as an elongated hollow tube. The orifice may be part of a nozzle. It is obvious to those skilled in the art that the overall design of the nozzle may have to be optimized for process stability. Furthermore, the central fluid stream may be concentric or eccentric. A fiberizing fluid, such as a central fluid stream, is blown to form an elongated hollow tube. The fiberizing fluid will then provide pressure on the inner surface of the elongated hollow tube. Thinned wall or weakened portions may form in the hollow tube to more easily and controllably enable the formation of fibers, including nanofibers. The weakened portions may result from notches or projections located on the outer surface of the central fluid jet tube or on the inner surface of the polymer extrusion orifice. The elongated hollow polymeric film tube is then subjected to a fluid to form the nanofibers. This fluid can be the central fluid stream or an entraining fluid or any fluid stream to induce a pulsating or fluctuating pressure field and forms a multiplicity of fibers, including nanofibers. If advantageous, a nozzle providing cooling or heating fluid to the formed nanofibers may be used.

The polymer is typically heated until it forms a liquid and flows easily. The melted polymer may be at a temperature of from about 0° C. to about 400° C., preferably from about 10° C. to about 300° C., and more preferably from about 20° C. to about 220° C. The temperature of the polymer depends on the melting point of the polymer or polymer composition. The temperature of the polymer is less than about 50° C. above its melting point, preferably less than 25° C. above its melting point, more preferably less than 15° C. above its melting point, and just at or above its melting point or melting range. The melting point or range is measured using ISO 3146 method. The melted polymer will typically have a viscosity of from about 1 Pa-s to about 1000 Pa-s, typically from about 2 to about 200 Pa-s and more commonly from about 4 to about 100 Pa-s. These viscosities are given over a shear rate ranging from about 100 to about 100,000 per second. The melted polymer is at a pressure of about atmospheric pressure or slightly elevated.

The elongated hollow polymer tube can be circular, elliptical, irregular, or any other shape which has a hollow region. In some cases, the elongated hollow polymer tube may collapse immediately after forming. In the case of the collapsed tube, it may be preferred to have thinned walls or weakened portions in the tube to aid in the fibrillation. Non-limiting examples of the fiberizing fluid are gases such as nitrogen or more preferably air. The fiberizing fluid is typically at a temperature close to the temperature of the melted polymer. The fiberizing fluid temperature may be a higher temperature than the melted polymer to help in the flow of the polymer and the formation of the hollow tube. Alternatively, the fiberizing fluid temperature can be below the melted polymer temperature to assist in the formation and solidification of the nanofibers. Preferably the fiberizing fluid temperature is less than the polymer melting point, more preferably more than 50° C. below the polymer melting point, more preferably more than 100° C. below the polymer melting point, or just at ambient temperature. The pressure of the fiberizing fluid is sufficient to fibrillate the nanofibers and can be slightly above the pressure of the melted polymer as it is extruded out of the orifice.

The fiberizing fluid may have a velocity of less than about 500 meter per second. Preferably, the fiberizing fluid velocity will be less than about 100 meter per second, more preferably less than about 60 meter per second, and most preferably from about 10 to about 50 meters per second. The fiberizing fluid may pulsate or may be a steady flow. Although it is critical that this fiberizing fluid is present to aid in the formation of the elongated hollow polymeric film tube, the amount of fluid in this stream may be very low.

The polymer throughput will primarily depend upon the specific polymer used, the nozzle design, and the temperature and pressure of the polymer. The polymer throughput will be more than about 1 gram per minute per orifice. Preferably, the polymer throughput will be more than about 10 gram per minute per orifice and more preferably greater than about 20 gram per minute per orifice. There will likely be several orifices operating at one time which increases the total production throughput. The throughput, along with pressure, temperature, and velocity, are measured at the die orifice exit.

The fibrillation and solidification of the fibers may occur before the fibers and fluid exit the orifice. Once the elongated hollow tube exits the orifice, the nanofibers are formed. Commonly, the formation of nanofibers occurs immediately upon exiting the orifice. One or more fluid streams are used to form the multiplicity of nanofibers. The fluid stream can be the central fluid stream, an entraining fluid, or any other fluid stream. An entraining fluid can be used to induce a pulsating or fluctuating pressure field to help in forming a multiplicity of nanofibers. The entraining fluid may be provided by a transverse jet which is located to direct the flow of entraining fluid over and around the hollow elongated tube and nanofiber forming region. The entraining fluid can have a low velocity or a high velocity, such as near sonic or super sonic speeds. An entraining fluid with a low velocity will typically have a velocity of from about 1 to about 100 meter per second and preferably from about 3 to about 50 meter per second. The temperature of the entraining fluid can be the same as the above fiberizing fluid, ambient temperature, or a higher temperature, or a temperature below ambient.

An additional fluid stream, a quench or heating fluid, can also be used. This additional fluid stream is located to direct fluid into the nanofibers to cool or heat the fibers. If the additional fluid is used as a quenching fluid, it is at a temperature of from about −50° C. to about 100° C. and preferably from about 10° C. to 40° C. If the additional fluid is used as a heating fluid, it is at a temperature of from about 40° C. to 400° C. and typically from about 100° C. to about 250° C. Any fluid stream may contribute to the fiberization of the polymer melt and can thus generally be called fiberizing fluids.

Any of the fluid streams, including the central fluid stream, an entraining fluid, or additional fluid stream, may contain a treatment, additive, coating, or other substance or particulate for changing the surface, chemical, physical, or mechanical properties of the fibers produced.

The nanofibers are laid down on a collector to form a web. The collector is typically a conveyor belt or a drum. The collector is preferably porous and vacuum may be applied to provide suction to aid fiber lay down on the collector. The distance from the orifice to the collector distance, commonly called die-to-collector distance (DCD), can be optimized for desired web properties. To reduce the amount of fiber bundling or roping, the DCD should be relatively low. This lower distance does not enable the fibers to have time to entangle, wrap around one another, or bundle. It may be desired to utilize more than one DCD used in a web, to change the DCD during production, or to have different beams with different DCDs. It may be desirable to form a web with different uniformities by changing the DCD.

After the elongated hollow film tube is formed, the tube or the nanofibers may alternatively be subject to an additional process that further promotes the formation of nanofibers. The further processing would occur immediately after formation of the elongated hollow polymeric film tube and before the nanofibers have solidified to still be considered a single step process. The additional processing can utilize one or more Laval nozzles to speed up the gas velocities to sonic and/or supersonic range. When polymer melt is exposed to such high gas velocities, it bursts into multiplicity of fine fibers. Examples of a Laval nozzle are described in Nyssen et al., U.S. Pat. No. 5,075,161, in which a method of bursting polyphenylene sulfide melt into fine filaments is disclosed. The Laval nozzle may be positioned just after the spinning nozzle when the elongated hollow polymeric film tube is produced. Alternatively, Laval nozzle could be positioned just after the nanofibers have formed to further reduce the fiber size. Polymer fibers can be produced by subjecting the polymer melt streams to drawing out and cooling to below the melt temperature by extruding them into a gaseous medium which flows essentially parallel to the polymer melt streams and attains sonic or supersonic speed. This simultaneous deformation and cooling gives rise to amorphous fine or extremely fine fibers of finite length. High speed fiber bursting minimizes the surface oxidation of the fibers. The spinning speed, melt temperature, and the position of the Laval nozzle are appropriately set to achieve only partial thermal oxidation of fine filaments at their surface.

Various processes and combination of processes can be used to make the webs of the present invention. Melt fiber bursting, as disclosed in WO 04/020722 by Sodemann et al., can be combined with melt film fibrillation of the present invention on two separate beams on a single line. Various aspects of melt fiber bursting can be incorporated into melt film fibrillation, such as producing fibers of different strengths and diameters to provide a desired combination of properties. Alternatively, aspects of melt film fibrillation can be included in other melt fibrillation processes to increase the throughput rate by utilizing a hollow elongated tube to form fibers. For example, the melt film fibrillation process of the present invention could be modified to include a Laval nozzle to aid in drawing down the fibers. Drawing down can aid in further attenuation and increase the strength of the fibers. This may be particularly preferred for high Tg polymers such as polyesters in which stress-induced crystallization happens at speeds in excess of 4000 m/min.

The nanofibers of the present invention are used to make nonwoven webs. The web is defined as the total nonwoven composite. A web may have one or several layers. A layer is the web or part of a web that is produced in a separate fiber lay down or forming step. The webs of the present invention will comprise one or more layers having a significant number of nanofibers having diameters of less than one micron. A significant number is defined as at least about 25%. The significant number of fibers can be at least about 35%, at least about 50%, or more than 75% of the total number of fibers in the layer. The web could have 100% of the fibers having a diameter of less than about one micron. The fiber diameters of the web are measured using a scanning electron microscope at a magnification of greater than about 500 times and up to about 10,000 times as needed for visual analysis. To determine if a significant number of fibers have diameters less than one micron, at least about 100 fibers and preferably more fibers must be measured. The measurements must occur at various regions throughout the layer. Sufficient sampling that is statistically significant must occur.

The fiber diameter of the remaining larger fibers, up to 75%, may have fiber diameters in any range. Typically, the larger fiber diameters will be just above one micron to about 10 microns.

Preferably, a significant number of fibers in a layer will have a fiber diameter of less than about 900 nanometer and more preferably from about 100 nanometers to about 900 nanofibers. The fibers may have a diameter of less than 700 nanometers and from about 300 to about 900 nanometers. The preferred diameters depend upon the desired use of the web. For process and product benefits, it may be desirable in some applications to have a significant number of fibers having a diameter of less than about one micron and a significant number of fibers having a diameter of greater than about one micron. The larger fibers may trap and immobilize the nanofibers. This may help to reduce the amount of clumping or roping of the nanofibers and prevents the nanofibers from being carried off by stray air currents.

The layers of nanofibers in a web of the present invention may contain more than one polymer. Different polymers or polymer blends may be used for different orifices to produce layers in a web having different fiber diameters and different polymer compositions.

It may be desirable to produce a single layer nonwoven with varying fiber diameters. Alternatively, it can be desired to produce a nonwoven web with multiple layers with each layer having different fiber diameters. The melt film fibrillation process can be modified to produce both small and large diameter fibers to make various webs. The smaller fiber diameters are referred to as having a significant number of fibers having a diameter of less than one micron. The larger diameter fibers include fibers from the melt blowing range (typically 3 to 5 microns) to the spunbond (typically around 15 microns) or any range of fiber diameters above 1 micron. For example, one layer can be produced with an average fiber diameter of less than one micron and another layer with an average fiber diameter of around 5 microns. This type of structure could be used where traditionally SMS webs are used. Another example is to produce a nanofiber web with multiple layers, with each layer having a distinct average fiber diameter such as one layer having an average fiber diameter of 0.4 micron and a second layer having an average fiber diameter of 0.8 micron. The webs with various fiber diameters can be produced on the same line with the same equipment. This is an inexpensive way as the same equipment and components can be used. The operating costs and equipment costs are both controlled. Also, if desired, the same polymer can be used to produce different fiber diameters.

It may be desired to form a web of several layers. The nanofiber layer may be combined with one, two or more layers. A spunbond-nanofiber-spunbond web is one example. Basis weights for the total composite webs range from about 5 gsm to about 100, preferably from about 10 to about 100 gsm, and more preferably from about 10 gsm to about 50 gsm. For use as a barrier layers, the total composite web basis weight may be from about 10 gsm to about 30 gsm. The basis weight of only the nanofiber layer is from about 0.5 gsm to about 30 gsm and preferably from about 1 gsm to about 15 gsm.

After the nonwoven is made, it may be subject to post processing. Nonlimiting examples of post processing include solid state formation, consolidation, lamination, surface coating, corona and plasma treatment, dyeing, and printing. Nonlimiting examples of solid state formation include processes using intermeshing rolls, such as in U.S. Pat. No. 5,518,801 and referred to in subsequent patent literature as "SELF" webs, which stands for "Structural Elastic-like Film", texturing, stretching, aperturing, laminating, local straining, micro creping, hydroforming, and vacuum forming. Nonlimiting examples of consolidation include thermal bonding, through air bonding, adhesive bonding, and hydroentangling.

The hygiene articles of the present invention will contain the above described nonwoven webs. The web may comprise the entire hygiene articles, such as a wipe, or the web may comprise one component of the hygiene article, such as a diaper. The hygiene articles include diapers, training pants, adult incontinence pads, catamenials products such as feminine care pads and pantiliners, tampons, personal cleansing articles, personal care articles, and hygiene wipes including baby wipes, facial wipes, body wipes, and feminine wipes. Personal care articles include articles such as wound dressings, active delivery wraps or patches, and other substrates that are applied to the body, particularly the skin.

In a diaper, the web may be used as a barrier layer or an outercover. The webs may also be used as a high barrier cuff with a high hydrostatic head to enable low leakage incident rates of thin, narrow crotch diapers desired for comfort and fit. The webs may be used in wipes to enable improved lotion handling and reduced gradient of liquids. The webs may also provide controlled delivery of a substance. The delivered substance can be of liquids, lotions, actives, or other materials. Due to the high surface area of the nanofibers, the webs may be used as absorbent materials for wipes or cores of feminine care product pads, diapers, training pants, or adult incontinence. The webs may provide enhanced distribution of fluids and/or retention. Additionally, the webs for absorbent uses may be made with added particulates or absorbent or natural fibers for increased absorbance or certain layers of the webs may have different properties. The nanofiber webs may also be used in articles wherein opaqueness is desired. Added opaqueness may result due to the small fiber diameter and uniformity; or pigments may be added to the polymer melt or webs. Commonly, the nanofiber layer is combined in a web with a spunbond layer. There may be one spunbond layer or a spunbond layer on each side of the nanofiber web.

In a diaper or other disposable absorbent product, the nonwoven web containing nanofibers may be utilized as a barrier layer. The barrier layer may be disposed between an absorbent core and an outer layer of the disposable absorbent product. The absorbent core is the component of the article that is primarily responsible for fluid handling properties such as acquiring, transporting, distributing, and storing body fluids. The absorbent core is typically located between a liquid pervious body-side inner layer and a vapor permeable, liquid impermeable outer cover. The outer layer, also known as the back sheet or outer covering, is located on the outside of the disposable product. In the case of a diaper, the outer layer contact the user's garment or clothing. The barrier layer may alternatively or also be disposed between the absorbent core and an inner layer. The inner layer, also known as a top sheet, is located on the side closest to the user's skin. The inner layer may contact the user's skin or may contact a separate top sheet with contacts the user's skin. The barrier layer may be absorbent. The nonwoven web may comprise the layer around the absorbent core and help to distribute or handle fluids. The nonwoven web may be a fluid distribution layer, which may be located adjacent to the core. The barrier layer most preferably has a balance between convective air flow and absorptive barrier property. The convective air flow property is effective to reduce the relative humidity within the space between the absorbent article and the wearer's skin. The combination of liquid absorption and liquid barrier property provides protection against the wet through problem and is especially beneficial when the absorbent article is under impact and/or sustained pressure. Further description and benefits of the barrier layers may be found in WO 01/97731.

The webs may be used to make hygiene wipes that are dry or pre-moistened. The nanofiber may be used in wipes to enable improved lotion handling and reduced gradient of liquids. The nanofiber layer may provide a partial barrier and may be partially or completely liquid impervious. The webs may also provide controlled delivery of a substance or active such as a drug. The delivered substance can be liquids, lotions, enzymes, catalysts, actives, or other materials such as emollients, surfactants, wetting agents, polishes, oils, organic and inorganic solvents, pastes, gels, pigments, or dyes. The webs may provide enhanced distribution of fluids and/or retention. Additionally, the webs for absorbent uses may be made with added particulates or absorbent or natural fibers for increased absorbance or certain layers of the webs may have different properties. The nanofibers may be produced to be low density or porous nanofibers. The nanofibers may be produced with an inflatent or blowing agent.

Due to the high surface area of the nanofibers, the webs may be used as absorbent materials for wipes or cores of feminine care product pads, diapers, training pants, or adult incontinence. The high surface area also enhances cleaning and may be used in hygiene cleaning wipes. The webs may provide enhanced distribution of fluids and/or retention. Additionally, the webs for absorbent uses may be made with added particulates or absorbent or natural fibers for increased absorbance or certain layers of the webs may have different properties.

The nanofiber webs may also be used in articles wherein opaqueness is desired. Added opaqueness may result due to the small fiber diameter and uniformity; or pigments may be added to the polymer melt or webs. The webs may also be low linting resulting from longer length fibers or entangling of fibers in the web. The tensile strength of the nanofiber webs of the present invention can be greater than the tensile strength of webs with similar fiber diameters and similar basis weights made from other processes. The nanofiber webs of the present invention will be soft and may be softer than other webs with the same performance.

Other products that will benefit from a nanofiber web include a personal filter or mask such as a surgical mask. Other medical uses of webs containing nanofiber layers include surgical gowns, wound dressings, and medical barriers.

The fiber diameter can be measured using a Scanning Electronic Microscope (SEM) and image analysis software. A magnification of 500 to 10,000 is chosen such that the fibers are suitably enlarged for measurements. Image analysis software for automatic sampling of fiber diameter in the SEM picture is possible, but also a more manual procedure can be used. In general, the edge of a randomly selected fiber is sought and then measured across the width (perpendicular to fiber direction at that spot) to the opposite edge of the fiber. A scaled and calibrated image analysis tool provides the scaling to get the actual reading in mm or micrometers ($\mu$m). Several fibers are randomly selected across the sample of web in the SEM. Typically, several samples from a web are cut and tested in this manner and at least about 100 measurements are made and all data are recorded for statistic analysis. If the result is to be recorded in denier, then the following calculation needs to be made. Diameter in denier=Cross-sectional area*density*9000 m*1000 g/kg. The cross-sectional area is $\pi$*diameter$^2$/4. The density for PP, e.g., can be taken as 910 kg/m$^3$. To obtain decitex (dtex), the 9000 m is replaced by 10,000 m.

Basis weight can be measured consistent with compendial methods ASTM D 756, ISO 536 and EDANA ERT-40.3-90. Basis weight is defined as mass per unit area, with grams per square meter (gsm) as the preferred unit. Required instruments are a scissors or a die-cutter for sample cutting and an accurate weighing device, such as a scale. A sample is cut to a total area of 100 cm$^2$ per layer with an accuracy and precision of ±0.5%. A scale or balance is needed with 0.001 g sensitivity, readable, calibrated and accurate to within 0.25% of the applied load. The samples are conditioned at 23° Celsius (±2° C.) and at a relative humidity of about 50% for 2 hours to reach equilibrium. Weigh the cut sample with 10 plies from the sample area for a total of 1000 cm$^2$=0.1 m$^2$ on an analytical balance to the nearest 0.001 g and record the weight. (For samples thicker than 1 mm, weighing only 1 ply is preferred but should be noted.) Calculate the basis weight by dividing the weight by the sample area (all layers tested) to give the basis weight in gsm. All data are recorded for statistic analysis.

Web uniformity can be measured through several methods. Examples of uniformity metrics include low coefficient of variation of pore diameter, basis weight, air permeability, and/or opacity. Uniformity also requires lack of fiber bundles or roping, or visible holes, or other such defects. Uniformity can be controlled by process modification such as reducing the nozzle to collector distance. The reduction in this distance reduces the fiber bundling or roping and can provide more uniform webs.

Pore diameter can be determined by methods known to those skilled in the art. The mean pore diameter is preferably less than about 15 microns, more preferably less than about 10 microns, and most preferably less than about 5 microns. The desired coefficient of variation for a uniform web is less than 20%, preferably less than about 15%, and more preferably about 10% or less. The lack of roping can be measured by counting the number of ropes or bundles of fibers in a measured area of the web. The lack of holes is also measured the number of holes having a diameter above a certain threshold in a measured area of the web. The holes may be counted if they are visible to the naked eye or are more than 100 microns in diameter.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a nonwoven web comprising nanofibers, wherein said nanofibers are made by a melt film fibrillation process, said method of making the nonwoven web comprising the steps of:
   a. providing a polymer in the form of a polymeric melt;
   b. utilizing a central fluid stream to form an elongated hollow polymeric film tube from said polymeric melt;
   c. using a fluid to form multiple nanofibers from the hollow polymeric film tube; and
   d. laying said nanofibers on a collector to form a nonwoven web, wherein said nonwoven web comprises a layer comprising at least 25% nanofibers with diameters less than one micron, and wherein said nonwoven web has a mean pore diameter of less than about 15 microns.

2. The method of claim 1 wherein the polymer is selected from the group consisting of polyolefins, polyesters, polyamides, biodegradable polymers, polyurethanes, polystyrenes, and combinations thereof.

3. The method of claim 2 wherein the polymer is polypropylene.

4. The method of claim 1 wherein the fluid used in step (c) is said central fluid stream.

5. The method of claim 1 wherein the fluid used in step (c) is another fluid stream.

6. The method of claim 1 wherein the layer comprises at least 35% of nanofibers having a diameter of less than one micron.

7. The method of claim 1 wherein the nanofiber layer has a basis weight of from about 0.5 gsm to about 30 gsm.

8. The method of claim 1 further comprising combining the layer of nanofibers with one or more layers of spunbond fibers to form a composite nonwoven web.

9. The method of claim 8 wherein the combined nonwoven web has a basis weight of from about 5 to about 100 gsm.

10. The method of claim 1 further comprising a step of:
e. incorporating said nonwoven web into a hygiene article.

11. The method of claim 10 wherein the hygiene article is selected from the group consisting of diapers, training pants, adult incontinence pads, catamenials products including feminine care pads and pantiliners, tampons, personal cleansing articles, personal care articles, and personal care wipes including baby wipes, facial wipes, body wipes and feminine wipes, and combinations thereof.

12. The method of claim 11 wherein the nonwoven web comprising the nanofibers is a fluid distribution layer.

13. The method of claim 11 wherein the hygiene article is a catamenial product, and the nonwoven web comprising the nanofibers is a fluid distribution layer.

14. The method of claim 11 wherein said hygiene article is a hygiene wipe.

15. The hygiene wipe of claim 14 wherein the nonwoven web comprising nanofibers provides a reduction of gradient of liquids.

16. The hygiene wipe of claim 14 wherein the nonwoven web comprising nanofibers provides controlled delivery of a material.

17. The method of claim 10 wherein said hygiene article is a diaper.

18. The method of claim 17 wherein the nonwoven web comprising nanofibers is a barrier layer.

19. The method of claim 18 wherein the barrier layer is an outercover.

20. The method of claim 18 wherein the barrier layer is a layer covering an absorbent core.

21. The method of claim 18 wherein the barrier layer comprises at least part of a leg cuff.

22. The method of claim 10 wherein the hygiene article is a catamenial product, and the nonwoven web comprising the nanofibers is a barrier layer.

* * * * *